United States Patent [19]

Dumas et al.

[11] Patent Number: 5,224,956
[45] Date of Patent: Jul. 6, 1993

[54] STATIC SPINAL ALIGNMENT DEVICE

[75] Inventors: Armen Dumas, Oxnard; Irving H. Plone, Playa del Rey; Bradley J. Zacuto, Van Nuys, all of Calif.

[73] Assignee: Pacific Medical Products, Encino, Calif.

[21] Appl. No.: 698,443

[22] Filed: May 9, 1991

Related U.S. Application Data

[63] Continuation of Ser. No. 333,333, Apr. 5, 1989, abandoned.

[51] Int. Cl.⁵ .............................................. A61F 5/02
[52] U.S. Cl. .................................... 606/240; 606/241
[58] Field of Search .................................... 128/69–71, 128/78, 870, 845; 272/144; 602/32; 606/237–240; 5/466, 630, 632, 633, 646, 648, 725; 482/142

[56] References Cited

U.S. PATENT DOCUMENTS

| 726,054 | 4/1903 | Hartford . |
| 744,713 | 4/1903 | Blanqvist . |
| 1,904,039 | 4/1933 | Bruder . |
| 1,934,918 | 11/1933 | Everson . |
| 3,861,666 | 1/1975 | Nishiyama et al. ............ 128/870 X |
| 3,889,664 | 6/1975 | Heuser et al. . |
| 3,955,285 | 5/1976 | Moeckl . |
| 4,071,031 | 1/1978 | Lowman ............... 128/DIG. 20 X |
| 4,210,134 | 7/1980 | Okazaki et al. . |
| 4,230,099 | 10/1980 | Richardson . |
| 4,326,534 | 4/1982 | Axelgaard et al. . |
| 4,342,317 | 8/1982 | Axelgaard . |
| 4,362,151 | 12/1982 | Cottrell . |
| 4,367,870 | 1/1983 | Birch . |
| 4,408,609 | 10/1983 | Axelgaard . |
| 4,475,542 | 10/1984 | Brossard . |
| 4,483,329 | 11/1984 | Shamos . |
| 4,559,979 | 7/1984 | Lewis, Jr. . |
| 4,597,386 | 7/1986 | Goldstein . |
| 4,621,809 | 11/1986 | Pearl . |
| 4,723,557 | 2/1988 | Gross . |
| 4,750,478 | 6/1988 | Bergeron . |
| 4,756,090 | 7/1988 | Pedrow . |

Primary Examiner—Richard J. Apley
Assistant Examiner—Linda C. Dvorak
Attorney, Agent, or Firm—Poms, Smith, Lande & Rose

[57] ABSTRACT

According to the present invention, a static or passive spinal alignment device includes a first elongated section and a second elongated section spaced therefrom. The first section and the second section are each dimensioned to buttress a respective side of a patient lying supine on a generally flat surface. The side buttressing straightens the alignment of the spine and maintains the spine of the patient in a spaced relationship to the surface between the thoracic vertebra and a sacrum of the spine. Body weight then urges the spine downwardly to reduce lumbar lordosis. Means are provided for attaching the first section to the second section and for supporting each of the first section and the second section on the surface.

16 Claims, 2 Drawing Sheets

STATIC SPINAL ALIGNMENT DEVICE

This is a continuation of copending application Ser. No. 07/333,333 filed on Apr. 5, 1989, now abandoned.

BACKGROUND OF THE INVENTION

1. Field of Invention

The present invention relates generally to orthopedic devices, and more particularly to a novel back alignment device which utilizes static side buttressing to straighten the alignment of the spine and further to reduce lumbar lordosis.

2. Description of the Related Art

In the treatment of back pain, it is necessary to straighten the alignment of the spine while reducing lumbar lordosis. Traction devices have been used for many years in such treatment. A traction device typically flattens the lumbar spine to overcome the anatomical lordosis. In one known traction device, the buttocks of a patient are cradled and lifted so that the patient's own weight provides a traction force to overcome the lumbar lordosis. For example, see U.S. Pat. No. 4,362,151. A significant disadvantage and limitation of such a traction device is that it requires the patient to be confined to a bed so that the cradle can be supported by ropes and pulleys with the appropriate counter-balances.

Ambulatory traction devices are also known. For example, in U.S. Pat. No. 3,889,664, a surgical brace device for ambulatory treatment of the lower back is disclosed. The device disclosed therein includes a pair of spaced apart torso belt members joined together with jack screw connecting means for applying traction to the user between the pair of belts. The device further includes a pair of adjustably spaced lordosis pads mounted on the lower belt. These pads apply forward pressure on spaced apart back vertebra.

A disadvantage and limitation of each of the above described traction devices is that they are active devices which require trained personnel to position the patient in the device or apply the device around the patient. It is highly desirable to provide a "static" approach wherein the patient can use the device at home without any special expertise or knowledge of device set up.

A typical home remedy for sufferers of back pain is to lie on a floor or some other hard surface to obtain relief. However, while lying on a floor can reduce lumbar lordosis, it cannot ensure alignment of the spine. Reducing lumbar lordosis without spinal alignment can, in fact, cause more pain and damage than relief because of the potential to apply unwanted stress on the joints, increase disc pressure and pinch the nerve roots emanating from the spinal cord.

Static devices for home remedies are also known. For example, in U.S. Pat. No. 4,597,386, there is disclosed a lumbar support system which is attached to the backrest of a chair. The lumbar support flexes curvilinearly to match the curve of the lumbar lordosis. A disadvantage and limitation of such a lumbar support is that, while providing lumbar support, it does not straighten the alignment of the vertebra of the spine.

Another device and method for the reduction of lumbar lordosis is described in U.S. Pat. No. 4,483,329. This device is positioned between a flat surface and a patient lying supine on the surface. The support device is positioned in the sacral area of the patient to support the apex of the patient's sacrum without providing support for the base of the patient's sacrum. The patient's body weight displaces the sacral base posterially and displaces the apex anteriorly to reduce lumbar lordosis. A disadvantage and limitation of the device described in the '329 patent is that it still does not straighten the alignment of the spinal vertebra.

SUMMARY OF THE INVENTION

According to the present invention, a static or passive spinal alignment device includes a first elongated section and a second elongated section spaced therefrom. The first section and the second section are each dimensioned to buttress a respective side of a patient lying supine on a generally flat surface. The side buttressing maintains the spine of the patient in a spaced relationship to the surface between the thoracic vertebra and a sacrum of the spine and further straightens the alignment of the spine. Means are provided for attaching the first section to the second section and for supporting each of the first section and the second section on the surface.

A feature of the present invention is that body weight exerts a downward force on the lumbar vertebra to reduce lumbar lordosis while the side buttressing straightens the alignment of the spine. Such a device may, in one embodiment of the present invention, be of unitary construction so that it is small, light and portable enough for use in the home.

These and other objects, advantages and features of the present invention will become apparent from a study of the following description of the preferred exemplary embodiment when read in conjunction with the attached drawings, and the scope of the present invention given by the appended claims.

DESCRIPTION OF AN EXEMPLARY PREFERRED EMBODIMENT

Figure 1:
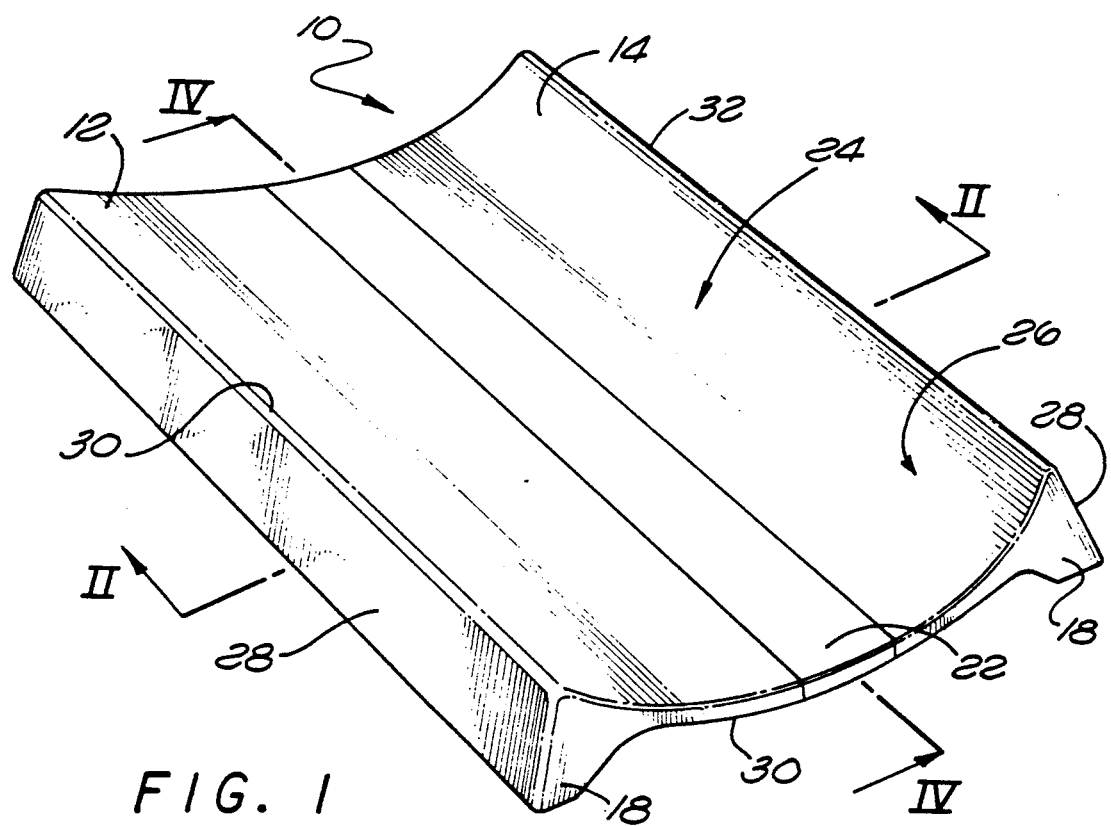
FIG. 1 is a perspective view of a static spinal alignment device constructed according to the principles of the present invention.
Figure 2:
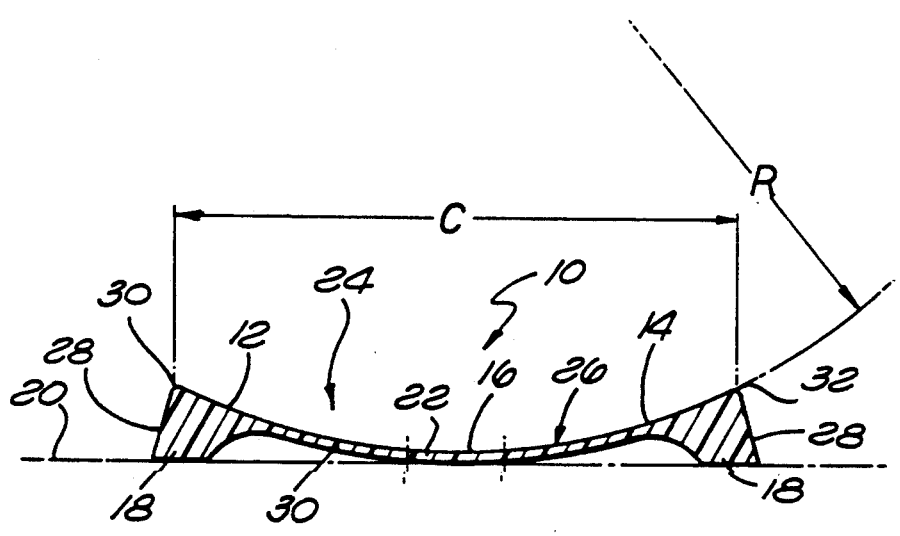
FIG. 2 is a cross-sectional view of the static spinal alignment device taken along line II—II of FIG. 1.

Referring now to FIGS. 1 and 2, there is shown a static or passive spinal alignment device 10 constructed according to the principles of the present invention. The spinal alignment device 10 includes a first elongated section 12 and a second elongated section 14 spaced therefrom, means 16 attaching the first section 12 to the second section 14 and means 18 for supporting each of the first section 12 and the second section 14 on a surface 20.

Attaching means 16 includes, a third elongated section 22 co-extensive with and attached to each of the first section 12 and the second section 14 intermediately therewith. Each of the first section 12, the second section 14, and the third section 22 form a generally elongated member 24. Member 24 has an inner surface 26 having a selected radius, R, of curvature as best seen in FIG. 2. Thus, the member 24 is axially elongated and arcuate.

Supporting means 18 includes a pair of axially extending pedestals 28. Each of the pedestals 28 are co-extensive with and support the respective one of the first section 12 and the second section 14. An outer surface 30 of the arcuate member 24 is supported by the flat surface 20 axially along the third section 22.

The static spinal alignment device 10, as hereinabove described, may be of unitary construction. The axially elongated arcuate member 24 may have a length in a range between 20 inches (50.8 centimeters) and 28 inches (70.1 centimeters). In a preferred embodiment of the present invention, the length of the member 24 is 24 inches (61.0 centimeters). The radius of curvature, R, is in a range between 16 inches (40.6 centimeters) and 20 inches (50.8 centimeters). In a preferred embodiment of the present invention, the radius of curvature, R, is 18 inches (45.7 centimeters). The distance along a cord, C, between an axial lateral edge 30 of the first section 12 and an axial lateral edge 32 of the second section 14 may be in a range between 15 inches (38.1 centimeters) to 17 inches (43.2 centimeters). In a preferred embodiment of the present invention, this distance along the cord, C, between the lateral edge 30 and the lateral edge 32 of the first section 12 and second section 14, respectively, is 16 inches (40.6 centimeters). Each of the first lateral edge 30 and second lateral edge 32 of the first section 12 and second section 14, respectively, are identically elevationally spaced from the flat surface 20 in a range of 1.5 inches (3.81 centimeters) to 2.5 inches (6.35 centimeters). In a preferred embodiment of the present invention, these lateral edges 30, 32 are elevationally spaced from the surface 20 by a distance of 2 inches (5.08 centimeters).

Figures 3A, 3B:
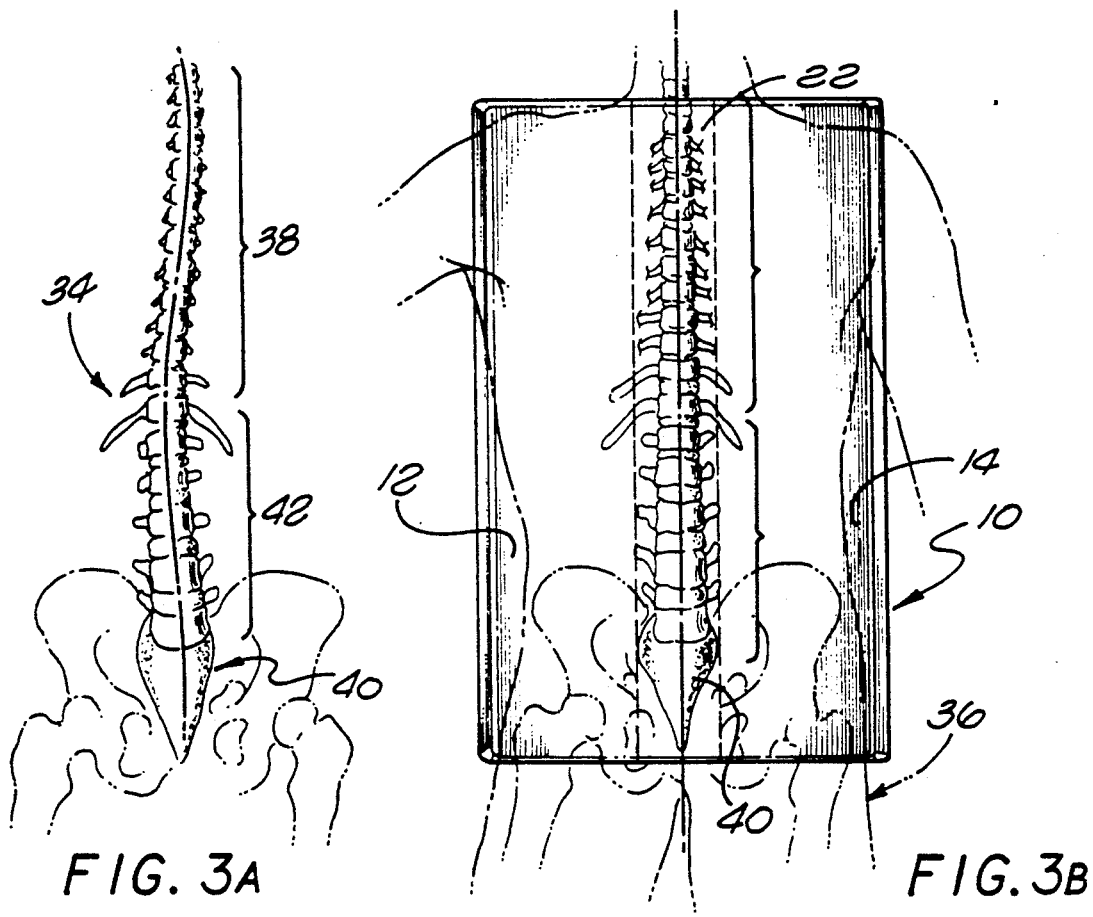
FIGS. 3A and 3B exhibit axial spinal misalignment (FIG. 3A) and axial spinal alignment (FIG. 3B) achieved by using the device of FIG. 1 shown in top view.

Referring now further to FIGS. 3A and 3B, a spine 34 of a patient 36 is, as best seen in FIG. 3A, shown to be misaligned, such as when the patient 36 may be lying on the flat surface 20, without using the device 10 of the present invention. With particular reference to FIG. 3B, the first section 12 and the second section 14 of the static spinal alignment device 10 engages each side of the patient 36 lying supine on the flat surface 20 to straighten the alignment of the spine 34. The static spinal alignment device 10, and more particularly the first section 12 and second section 14 are positioned to achieve side buttressing of the spine including and between the thoracic vertebra 38 and the sacrum 40 of the spine. As best seen in FIG. 3B, the spine 34 is then straightened and aligned with the third section 22 of the spinal alignment device 10.

Figure 4A:
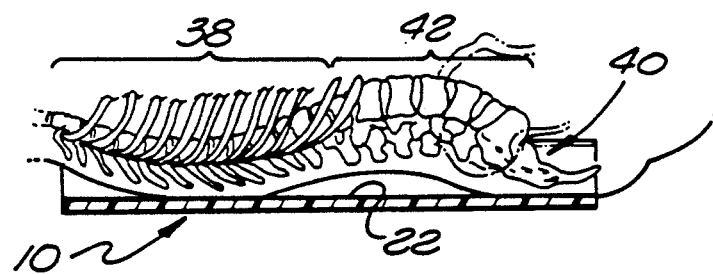
FIGS. 4A and 4B illustrate the reduction of lumbar lordosis by use of the device of FIG. 1 shown in cross-section taken along line IV—IV of FIG. 1.
Figure 4B:
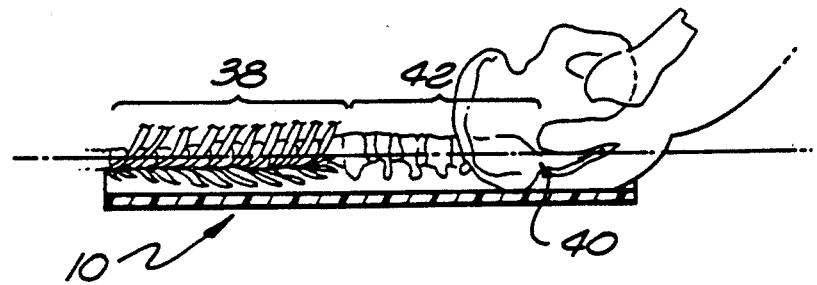

As best seen in FIGS. 4A and 4B, as the patient 36 lies in the static spinal alignment device 10 and is supported by the first section 12 and second section 14, the lumbar vertebra 42 between the thoracic vertebra 38 and sacrum 40 are spaced from the third section 22. In FIG. 4A, the lumbar vertebra 42 are shown with an extreme lumbar lordosis. As best seen in FIG. 4B, the body weight of the patient 36 reduces the lumbar lordosis, while maintaining it in alignment from the side buttressing as described hereinabove. The side buttressing provided by the first section 12 and second section 14 exerts pressure on the patient laterally inwardly in response to the body weight of the patient to maintain the alignment of the spine 34. The body weight of the patient urges the straightened spine 34 downwardly to reduce the lumbar lordosis.

There has been described hereinabove a novel static spinal alignment device constructed according to the principles of the invention to achieve simultaneously straightening the alignment of the spine and the reduction of lumbar lordosis. It is apparent that those skilled in the art may now make numerous uses of and departures from the present invention without departing from the inventive concepts herein. Accordingly, the present invention is to be defined solely by the scope of the following claims.

I claim:
1. A static spinal alignment device comprising:
   a. a first semi concave curved elongated section and a second semi concave curved elongated section spaced therefrom to accommodate a human being's back, each semi concave curved elongated section having a predetermined radius of curvature, said radius of curvature in a range between 16 inches and 20 inches, said first section and said second section each having an upper surface and a lower surface; each being dimensioned to buttress a respective side of a patient lying supine on a generally flat surface to maintain a spine of the patient in a spaced relationship to the surface between a thoracic vertebra and a sacrum of the spine and further to allow the patient's body weight to exert a downward force on the spine while said side buttressing straightens the alignment of the spine;
   b. means for attaching said first section to said second section, said attaching means having an axially elongated central portion, said central portion being substantially planar and lying in a plane substantially parallel to the surface, and further wherein said central portion is dimensioned in axial length so as to extend below the thoracic vertebra, the lumbar vertebra, and the sacrum of the patient; and
   c. means for supporting each of said first section and said second section on the flat surface.

2. A device as set forth in claim 1 wherein said attaching means includes:
   a. a substantially flat third elongated section having a uniform horizontal height co-extensive with and attached to the lower surfaces of each of said first section and said second section.

3. A device as set forth in claim 2 wherein each of said first section, said second section and said third section form a generally elongated substantially smooth concave member where said first and second sections are uniform in height.

4. A device as set forth in claim 3 wherein said device is of unitary construction.

5. A static spinal alignment device comprising:
   an axially elongated arcuate member having an inner surface having a radius of curvature, a first semi concave curved axially extending section having an upper and a lower surface, a second semi concave curved axially extending section having an upper and a lower surface and a third axially extending section intermediate said lower surfaces of said first section and said second section, said third section having an axially elongated central portion, said central portion being substantially planar and dimensioned in axial length so as to extend below the thoracic vertebra, the lumbar vertebra, and the sacrum of the patient, said inner surfaces of said member having a radius of curvature between 16 inches and 20 inches, wherein said first section and said second section engage a patient's back when said third section is positioned in general alignment with and spaced from a spine of the patient between a sacrum and thoracic vertebra of the spine and further to allow the patient's body weight to exert a downward force on the spine to straighten the alignment of the spine.

6. A device as set forth in claim 5 further comprising means for supporting said member on a generally flat surface, wherein said inner surface of said member faces away from the flat surface.

7. A device as set forth in claim 6 wherein said supporting means includes a pair of axially extending pedestals, each of said pedestals being co-extensive with and supporting a respective one of said first section and said second section.

8. A device as set forth in claim 7 wherein said member further has an outer surface, said outer surface being supported by the flat surface axially along said third section.

9. A device as set forth in claim 7 wherein said device is of unitary construction.

10. A device as set forth in claim 6 wherein said first section and said second section each have a lateral axially extending edge, said edge of each said first section and said second section being spaced elevationally from the surface in the range between 1.5 inches to 2.5 inches.

11. A device as set forth in claim 5 wherein said member has an axial length in a range between 20 inches and 28 inches.

12. A device as set forth in claim 5 wherein said first section and said second section each have a lateral axially extending edge wherein a distance along a cord between each said lateral edge is in a range of 15 inches and 17 inches.

13. A static spinal alignment device positional between a flat surface and a person lying supine on the surface, said device being positioned between a thoracic vertebra and a sacrum of the patient, said device comprising:

a. an axially elongated arcuate member having an inner surface having a radius of curvature and a facing relationship to the patient, a first semi concave curved axially extending member engaging a first side of the patient, a second semi concave curved axially extending member engaging a second side of the patient, said first section and said second section each having an upper surface and a lower surface and a third axially extending surface extending intermediate the lower surfaces of said first section and said second section and being generally co-extensive with and spaced from a spine of the patient, said first section and said second section each having a lateral axially extending edge wherein a distance along a cord between each said lateral edge is in a range of 15 inches and 17 inches, said third section having an axially elongated central portion, said central portion being substantially planar and lying in a plane substantially parallel to said surface, and further wherein said central portion is dimensioned in axial length so as to extend below the thoracic vertebra, the lumbar vertebra, and the sacrum of the patient; and said first section and said second section exerting pressure on the patient laterally inwardly in response to body weight of the patient to straighten the alignment of the spine, the body weight of the patient urging the spine downwardly toward said third section to reduce lumbar lordosis; and b. means for supporting said member on the flat surface.

14. A device as set forth in claim 13 wherein said supporting means includes a pair of axially extending pedestals, each of said pedestals being co-extensive with and supporting a respective one of said first section and said second section.

15. A device as set forth in claim 14 wherein said member further has an outer surface, said outer surface being supported by the flat surface axially along said third section.

16. A device as set forth in claim 15 wherein said device is of unitary construction.

* * * * *